United States Patent
Hartman (10) Patent No.: US 9,911,036 B2
(45) Date of Patent: Mar. 6, 2018

(54) FOCUSING METHOD FOR OPTICALLY CAPTURING AN IRIS IMAGE

(71) Applicant: AOptix Technologies, Inc., Campbell, CA (US)

(72) Inventor: Keith W. Hartman, Redwood City, CA (US)

(73) Assignee: Tascent, Inc., Los Gatos, CA (US)

( * ) Notice: Subject to any disclaimer, the term of this patent is extended or adjusted under 35 U.S.C. 154(b) by 578 days.

(21) Appl. No.: 13/783,838

(22) Filed: Mar. 4, 2013

(65) Prior Publication Data

US 2014/0132749 A1     May 15, 2014

Related U.S. Application Data (60) Provisional application No. 61/726,359, filed on Nov. 14, 2012.

(51) Int. Cl.
```
G06K 9/00      (2006.01)
A61B 3/113     (2006.01)
A61B 1/04      (2006.01)
H04N 7/18      (2006.01)
```

(52) U.S. Cl.
CPC .......... *G06K 9/00604* (2013.01); *A61B 1/041* (2013.01); *A61B 3/113* (2013.01); *H04N 7/18* (2013.01)

(58) Field of Classification Search
CPC .......... A61B 3/113; A61B 1/041; H04N 7/18; G06K 9/00604
See application file for complete search history.

(56) References Cited

U.S. PATENT DOCUMENTS

| | | | | | |
|---|---|---|---|---|---|
| 5,797,049 | A | * | 8/1998 | Ohtaka | G02B 7/34 396/111 |
| 6,120,461 | A | * | 9/2000 | Smyth | A61B 3/113 348/E13.041 |
| 6,370,265 | B1 | * | 4/2002 | Bell | G06T 5/009 345/589 |
| 7,123,779 | B2 | * | 10/2006 | Beuker | A61B 6/5241 382/284 |
| 8,025,399 | B2 | * | 9/2011 | Northcott | G06K 9/00604 351/200 |

(Continued)

OTHER PUBLICATIONS

PCT International Search Report and Written Opinion, PCT Application No. PCT/US2013/029247, dated May 10, 2013, nine pages.

*Primary Examiner* — Shawn An
(74) *Attorney, Agent, or Firm* — Fenwick & West LLP (57) ABSTRACT

Methods and systems describe calculating an estimated focal point for a feature of interest within an ocular area of a subject using acquired test images and focal points. A curve is approximately fit to the defocus measurements located at different focal points. A maximum of the curve is identified that corresponds to an estimated focal point of the subject's iris. An image capture device can then record an approximately focused image of the iris using the estimated focal point. This reduces the time and computing resources needed to capture an image iris that is in focus where the subject may be located at a variable, unknown standoff distance. These methods and systems can be used for biometric identification using iris imaging, among other applications where quickly focusing an imaging system is advantageous.

34 Claims, 3 Drawing Sheets

(56) References Cited

U.S. PATENT DOCUMENTS

| | | | |
|---|---|---|---|
| 2006/0066738 A1* | 3/2006 | Hershey | H04N 5/33 348/273 |
| 2007/0146635 A1* | 6/2007 | LeBlanc | A61B 3/113 351/221 |
| 2009/0046298 A1* | 2/2009 | Betzig | G01N 21/6445 356/521 |
| 2009/0168017 A1* | 7/2009 | O'Hara | A61B 3/102 351/205 |
| 2010/0165293 A1* | 7/2010 | Tanassi | A61B 3/117 351/208 |
| 2010/0201798 A1* | 8/2010 | Ren et al. | 348/78 |
| 2010/0220285 A1* | 9/2010 | Simmonds | G02C 13/005 351/204 |
| 2010/0220288 A1* | 9/2010 | Cleveland | A61B 3/113 351/206 |
| 2010/0259723 A1* | 10/2010 | Korb | A61B 3/0025 351/206 |
| 2010/0303294 A1* | 12/2010 | Zschau | A61B 3/113 382/103 |
| 2011/0293190 A1* | 12/2011 | O'Callaghan | G06T 7/20 382/197 |

* cited by examiner

FOCUSING METHOD FOR OPTICALLY CAPTURING AN IRIS IMAGE

CROSS REFERENCE TO RELATED APPLICATIONS

This application claims the benefit of U.S. Provisional Application No. 61/726,359, filed Nov. 14, 2012, which is incorporated by reference in its entirety.

BACKGROUND

1. Technical Field

The present disclosure relates to imaging facial features. Specifically, the present disclosure relates to a focusing method for optically capturing an iris image.

2. Description of Related Art

Imaging of a human iris is often performed by illuminating a spatial volume that includes the face of a subject and then recording an image of an illuminated iris. Infra-red light is often used for illumination because pigmentation in the iris is more transparent in the infra-red spectrum. The transparency of the pigmentation exposes the fine structures of the iris to the imaging system.

Iris images are useful for performing biometric identification. Iris-based biometric identification typically requires a spatial resolution of 200 microns, or better, with a pixel resolution of approximately 60 microns for an ISO standard 19794-6-compliant image. In general, higher spatial resolution leads to better matching performance by better distinguishing the fine muscle structure of human irises.

Illumination systems used for iris imaging, particularly biometric imaging, regularly comprise multiple illumination sources that flood the ocular areas (i.e., the areas surrounding and including the eyes of the subject) with a uniform or near uniform intensity of light. This type of arrangement facilitates adequate illumination of the ocular area and any irises within the ocular area.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

The system described below is used for quickly focusing an image capture device to record an image of an iris. Quickly focusing the image capture device is particularly useful when an iris image will be used for biometric identification. By quickly focusing the image capture device, the iris image of even uncooperative subjects can be captured and used for identification. Quick capture speeds the entire capture process by limiting the possibility of needing to recapture due to blinking or moving of the subject, or due to the effects of motion caused by the operator of the device. In one embodiment, an iris image can be captured in approximately 0.3 to 1.2 seconds. Iris images can be capture from a subject located any distance from the image capture system up to about 500 mm. The subject need not be positioned at a known or pre-determined location from the image capture device.

In one embodiment, calculation of an estimated focal point of an iris includes determining a defocus measurement for various test images recorded at corresponding measurement positions. A curve is approximately fit to the defocus measurements of the various test images and a maximum of the curve is identified. This maximum corresponds to an estimated focal point of the iris of the subject being imaged. The image capture device can then record an approximately focused image of the iris using the estimated focal point without using complicated image analysis algorithms. This reduces the time and computing resources needed to capture an image that is in focus. While the example embodiments described below are for iris imaging, it will be appreciated that the methods and systems of the present disclosure can be applied to the imaging of any type of subject, not only irises or facial features.

Figure 1A:
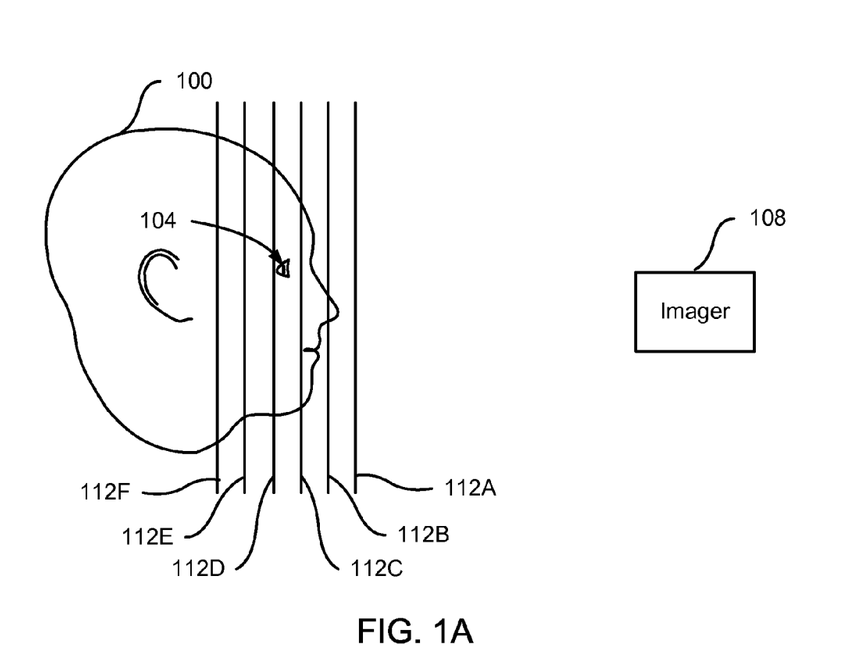
FIG. 1A is a side-view illustration of a plurality of focal points at which a plurality of test images are captured with respect to a face of a subject, in an embodiment.
Figure 1B:
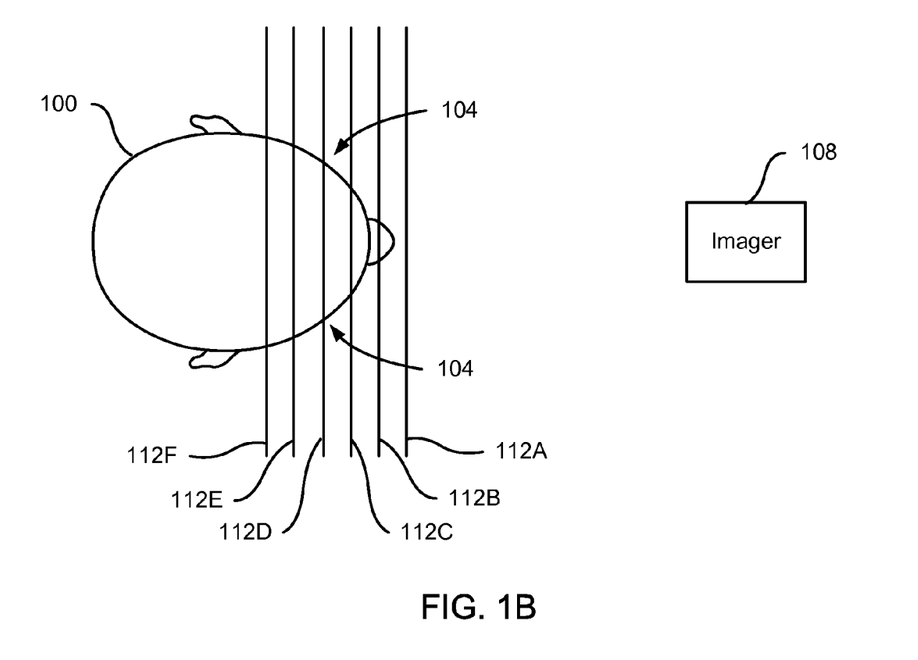
FIG. 1B is a plan-view illustration of a plurality of focal points at which a plurality of test images are captured with respect to a face of a subject, in an embodiment.

FIGS. 1A and 1B are different illustrations of a system that captures images of irises, in one embodiment. In these schematic illustrations, a subject 100, and more specifically the ocular areas 104 surrounding and including the eyes of the subject, are imaged by an imaging system 108. At a high level, the imaging system 108 acquires images of the subject 100 used for focusing ("test images") at various measurement positions 112A-112F by adjusting a focal length of an optical element (e.g., a lens) of the imaging system. This process is repeated any number of times, but typically at least three different test images are captured, each at a different measurement point, for reasons described below in the context of FIGS. 2 and 3.

Figure 3:
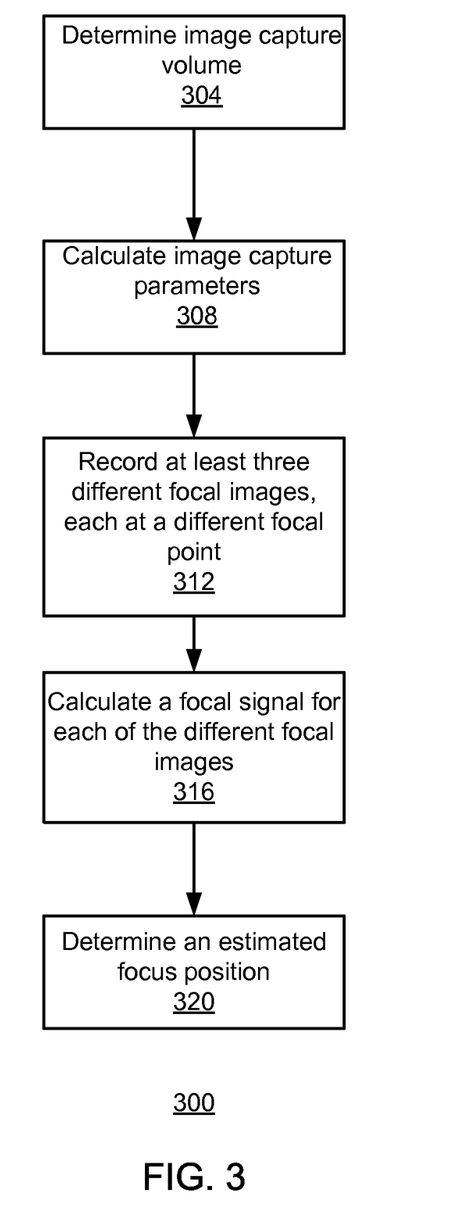
FIG. 3 is an example method for calculating an estimated focal point of the iris using a plurality of test images captured at a plurality of focal points, in an embodiment.

Upon acquiring the test images of the ocular areas 104 at the various measurement positions 112A-112F, the imaging system 108 calculates an estimated focal point for the iris(es) with the ocular area(s) 104 using a method described in the context of FIG. 3. This allows the estimated focal point for the ocular areas 104 to be determined quickly, providing for the rapid capture of a focused image of an iris within an ocular area 104 of a subject 100 without resorting to focusing software that is computationally intensive and comparatively time consuming.

Imaging System

Figure 2:
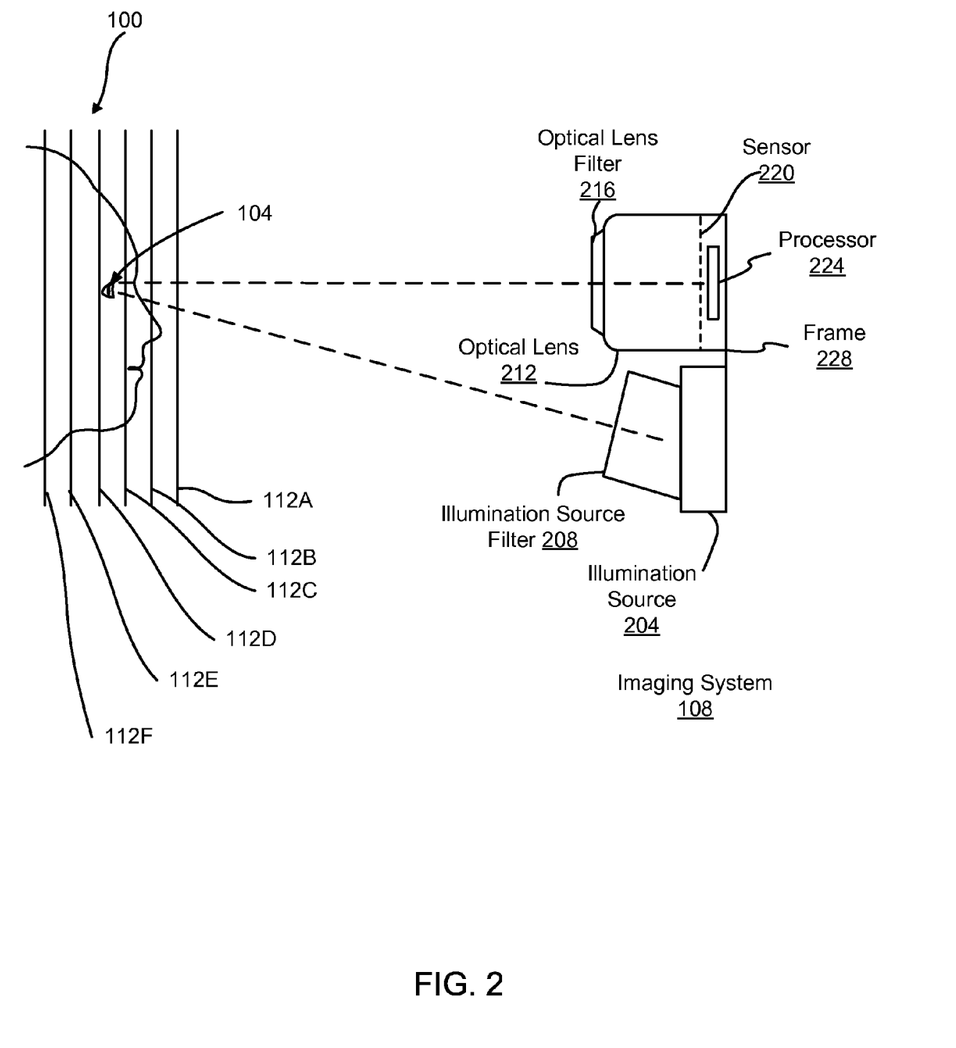
FIG. 2 is an example of a system for capturing a plurality of test images at a plurality of focal points and for calculating an estimated focal point of the iris, in an embodiment.

Turning now to FIG. 2, one embodiment of the imaging system 108 used for capturing iris images is shown. The system is configured to illuminate the ocular areas 104 that include the irises of the subject using infrared illumination, quickly bring the irises into focus, and capture the focused image. The imaging system 108 includes an illumination source 204, an optional illumination source filter 208, a face camera 210 (not shown), an optical lens 212, an optical lens filter 216, an image sensor 220, a processor 224, and an optional frame 228.

The illumination source 204 of the imaging system 108 produces illumination in the infra-red region of the light spectrum to better resolve the fine musculature structures of the iris. In some examples, this infra-red illumination includes wavelengths of light from approximately 700 nm to approximately 900 nm, although other wavelengths can be used as a function of the subject being imaged or the image sought. In some embodiments, the illumination source 204 is a semiconductor illumination device, such as one or more light emitting diodes ("LEDs"). In other examples, thermal illumination devices, such as electrically resistant filaments, can be used to produce illumination of the desired wavelength.

Furthermore, because the imaging system 108 is configured for imaging irises, the illumination source 204 can be configured to produce a dual-lobed irradiance or illumination distribution, wherein the lobes of the distribution are located approximately at the ocular areas 104 of a subject separated from the illumination sources by an approximate standoff distance. This standoff distance is the distance separating the imaging system 108 and the subject 100 being imaged, which for iris imaging examples, can be up to about 500 mm, depending on the specific configuration of the imaging system. This configuration can use any combination of lateral or angled separation of the two illumination sources 204, calculated using geometry principles, to produce the dual-lobed irradiance distribution at the standoff distance.

The illumination source 204 may also include an optional illumination source filter 208 for narrowing the wavelength of light emitted by the illumination source. This can allow for more efficient discrimination of extraneous background images from the iris image. For example, when used in cooperation with an optical lens filter, described below, ambient illumination can be suppressed, thereby emphasizing the corneal glints reflected from the eyes of the subject. These glints can be used as a focusing feature, further allowing for the rapid focusing the imaging system 108 by due to the glint's relatively high intensity and spatial gradient (e.g., as implemented by convolving Sobel gradient filter with an image) relative to anything else in the captured image.

In addition to the optional filters mentioned above, the illumination source 204 may also include an optional illumination source lens (not shown) to further focus, defocus, or otherwise direct light from the illumination source to the ocular areas 104 of a subject 100. The optional illumination lens can be used to tailor the shape and/or intensity of the light distribution at the standoff distance or at the various focal points 112A-F.

The face camera 210 (not shown) identifies a face of the subject 100 and, using facial recognition software in cooperation with the sensor 220 and the processor 224 (both described below), identifies the ocular areas 104 of the subject. Once the ocular areas 104 are identified, the coordinates of the ocular areas 104 are communicated to the processor 224 so that the other elements of the imaging system 108 (such as the optical lens 212, the sensor 220, and the processor 224) can zoom into the ocular areas 108, thereby capturing a focused image of an iris.

The optical lens 212 of the imaging system 108 is configured to receive an image (whether a test image or a focused image) of one or more irises disposed within an ocular area 104, identified by the face camera 210, at approximately the standoff distance, and to dynamically change the optical power (e.g., the inverse of the focal length of the imaging system, often quantified in diopters) of the lens to capture multiple test images at multiple measurement positions 112A-F. In one implementation, the optical lens 212 is a liquid lens that can vary the focal length of the optical lens 212 in nearly any increment by application of an electric field to the elements of the liquid lens. One advantage of the liquid lens 212 is its extremely fast focus-adjustment response time, approximately 20 milliseconds, compared to lenses using mechanical means to adjust the focus. This is particularly advantageous for capturing focused images of irises quickly for any subject, particularly for uncooperative subjects that may be resisting identification. Another optical element that can be focused as quickly and used in place of a liquid lens is a deformable mirror. Furthermore, the optical lens 212 may include, or be in optical communication with, a multi-element lens (not shown) used for zooming the field of view of the image capture device 108 to the ocular area. In one example, the field of view is a 256 pixel×256 pixel field of view, but other examples can have larger or smaller fields. This further facilitates using the imaging system 108 to record an image (whether a test image or a focused image) of an ocular area of a subject 100 at a standoff distance as far as approximately 500 mm.

The optical lens 212 partially or completely focuses received images onto the sensor 220. The sensor 220 is substantially disposed in the focal plane of the optical lens 212 and is substantially perpendicular to the optical axis of the imaging system, thereby allowing an image of the iris to be received by the sensor 220, described below.

An optical lens filter 216 can be placed in optical communication with the optical lens 212 and used for suppressing illumination from undesired sources or having undesired wavelengths. For example, the optical lens filter 216 can be used to exclude illumination from the ocular area(s) 104 of the subject 100 that are outside of the infra-red wavelengths provided by the illumination source 204. This reduces optical signals incoming to the optical lens 212 that either do not contribute to the resolution of the iris image or detract from the resolution of the iris image. In either case, using the optical lens filter 216 can help reduce the processing time of the image and reduce computing resources used to process the image received by the image sensor 220 because unwanted information is not received at the image sensor. This is in contrast to receiving unwanted information and then using the processor to reduce the effects on the image from the unwanted information, which increases the processing time needed to determine the estimated focal point.

In another example, the optical lens filter 216 is used to suppress other sources of illumination incident upon the system 108 and/or the subject 100 so that a corneal glint can be used for focusing. The intensity of light reflected by the cornea of an illuminated ocular area can be high. Particularly, due to the positioning of the illumination source, some light from the illumination source is reflected from a portion of the cornea. This reflected light is referred to as a corneal glint. The optical lens filter 216 can be used to suppress substantially all other light other than the corneal glint otherwise incident upon the lens 212, thereby accentuating the intensity of the glint relative to all other features captured in the test image. The corneal glint is used as a feature to assist in determining the estimated focal length, as described below in the context of FIG. 3. Other features of the test image, such as the edges between the sclera and the iris, or between the iris and the pupil can similarly be used as a feature to determine the focus of the test image, either alone or in conjunction with the corneal glint.

The sensor 220 receives the optical signal from the optical lens 212 and converts it into a signal that can be received by the processor 224. As explained below, the signal provided by the sensor 220 enables the processor 224 to record an image of the iris in a computer-readable medium, process the image, or biometrically identify the subject of the iris imaging, as described in more detail in the context of FIG. 3. Examples of the sensor 220 include a CMOS or a CCD sensor, although other similar sensors may also be used.

The processor 224 receives the coordinates of the ocular area 104 from the face camera 210, as well as images of the ocular areas from the sensor 220. The received images are processed according to the method described in FIG. 3. The processor can determine whether the image is in or out of focus based on the optical signal provided by the sensor 220 using, for example, the "sharpness" of a corneal glint (i.e., the number of pixels transitioning from a high intensity to a low intensity). Examples of the processor 224 include a field programmable gate array (FPGA), an application-specific integrated circuit (ASIC), or a computer processor that executes instructions stored in a non-transitory computer-readable medium.

The processor 224 calculates defocus measurements using test images received from the sensor 220. In one implementation, the processor 224 calculates a defocus measurement for each of the test images using a pixel intensity distribution of a corneal glint. As introduced above, the corneal glint can be the most prominent feature in the test images due to the substantial suppression of illumination other than that provided by the illumination source, as well as due to the high intensity and spatial gradient of the corneal glint compared to other features in the test image. In this case, an image sharpness algorithm is used on each test image as described below in the context of FIG. 3 to compute a defocus measurement for each test image. Regardless of the feature used to determine the focus, if the cornea is in focus, then it may be determined that the iris is in focus based on the depth of field of the lens 212 and sensor 220. Similarly, if the cornea is out of focus, then the focus of the iris can be determined based on the known distance between the surface of the cornea and the surface of the iris.

Focusing using this method uses relatively little processing time because prominent features, such as a glint or an edge between structures in the eye, have a relatively high signal to noise ratio in the received test image. Because of this high ratio, the processing of the test image can be done quickly and with a relatively low level of computational resources. This is in contrast to focusing methods using facial recognition or face-analysis algorithms, which may be computationally intensive.

The various components described above can be attached to (or held together) by an optional frame 228. Various embodiments of the frame 228 include an internal frame to which the components are attached to or an external frame which houses the various components.

The imaging system 108 may further include additional components that facilitate the receipt, processing, and transmission of images and/or data including, for example, a digital to analog converter, other processors, volatile and non-volatile memory, and/or a display.

Image Capture and Focus Method

FIG. 3 illustrates an example embodiment of a method 300 for focusing the imaging system 108 on an ocular area 104 of a subject. More specifically, the method 300 can be used by the imaging system 108 to quickly record an approximately focused image of the irises of the subject 100 with relatively low use of computational resources.

The imaging system 108 determines 304 an ocular area 104 of the subject 100 using the facial camera 210 (not shown) and facial recognition software executed by the processor 224 (or by another processor, i.e., a processor in a mobile computing device, such as an iPhone), which then analyzes the image using a face imaging algorithm to locate the ocular areas. The coordinates of the ocular areas are generated by face-finding software executed by a processor and are then used by the processor 224 to position the optical areas 104 in the field of view of the optical lens 212 (often 256 pixels×256 pixels) to capture the test images and ultimately the focused iris image. Alternatively, the imaging system 108 can be manually directed to an ocular area 104 by an operator. Image capture parameters are calculated 308 for the ocular area 104 by the imaging system 108 to configure the imaging system for quickly focusing the system on the irises of the subject and for resolving the fine musculature structures of the iris. In one implementation these parameters are used to configure the imaging system 108 to emphasize the corneal glints from the ocular areas of the subject used as focusing features in the test images. In another implementation, the image capture parameters are used to configure the system to capture the focused iris image at the estimated focal length.

The final iris image capture parameters may be calculated 308 by reference to previously captured images (for example, images taken proximate in time to the current image or under similar lighting conditions or both), by reference to prior information stored by the system, or by using data from the received test images, or from a preliminary "scout" exposure image. These parameters include, but are not limited to an intensity of the illumination source, sensor integration time, sensor gain, and combinations thereof. In some embodiments, the image capture parameters are calculated to minimize the sensor integration time (and reduce or minimize ambient noise), thereby reducing the overall time to capture a focused image of an iris. The image capture parameters for the focus image sequence may be different from that for the final iris capture image.

The image capture parameters are used to configure the imaging system to be able to capture images regardless of the ambient lighting conditions, whether indoor (having a generally lower ambient illumination intensity) or outdoor (possibly having a relatively high ambient illumination intensity). For example, regardless of the ambient lighting conditions, the imaging system 108 can be configured to emphasize the corneal glints, which usually have a high intensity and saturation, are the primary feature in the received image.

The processor 224 then computes capture parameters based on the current image and reference parameters. The reference parameters may be based on histograms or a reduced representation (such as mean, standard deviation, variance, or other statistical characterizations and descriptions) of the image histograms. By comparing the image features, the processor 224 can determine the image capture parameters that can be used for capturing the test images and the focused iris image at the estimated focal point.

In one embodiment, the processor 224 (in the example shown in FIG. 2, an FPGA) can apply the linear/non-linear transfer function described above to the recorded images using an off-the-shelf image manipulation program, such as PHOTOSHOP, although other computer-executable algorithms and instructions can also be used to achieve the same result. In other embodiments, additional processors or controllers can be used to perform this transformation.

The imaging system 108 records 312 at least three different test images at three different measurement positions (e.g., any of positions 112A-112F) of the subject's irises by adjusting a focal length of the optical lens 212. In one embodiment, an estimate of the allowed capture range (that is, the physical distance containing positions 112A-112F that is up to approximately 500 mm), constrained by optical quality requirements, is computed by the face-finding software. The optical quality requirements can be defined in terms of a modulation transfer function. That is, by imaging and recognizing the facial features of the subject 100, the imaging system 108 can determine the estimated first focal point of the imaging system in which the facial features of the subject 100 are approximately in focus. This area of the face of the subject 100 surrounding the ocular areas 104 in the 256×256 pixel data field also limits the incoming data to that most relevant to resolving the fine musculature structures of the iris.

In some embodiments, the test images are modified by a grayscale correction, which can be used to accentuate the edges in the image or improve the signal to noise ratio of a corneal glint, thereby enhancing the signal measured by the focusing algorithm described below. In captured iris images, generally the sclera of the eye may be partially or fully saturated, the pupil is partially or fully dark, and the iris is in between. To improve the captured image of the iris, for example when using a sensor 220 that records in color, a grayscale transformation can be applied so that the amplitude received from each pixel in the sensor, whether filtered by a red, blue, or green filter, produces a signal with a comparable amplitude. In another implementation, a grayscale transformation of an image is adjusted to be linear over the range of grayscale of the iris, and is adjusted to be nonlinear outside of that range (e.g., in the sclera and pupil regions). Effectively, this transfer function that is non-linear in areas of the eye having information of interest (e.g., the iris) and linear (e.g., either black or white) in areas that have less information of interest (e.g., the sclera and pupil) changes the contrast of the iris region to improve the detail of the captured iris, at the expense of losing detail in areas of the image that are not of interest (e.g., the sclera and pupil regions). In one embodiment, the image capture parameters are used to set the exposure of the image capture device.

In another implementation, an edge enhancement algorithm or an image sharpness algorithm is executed by the processor 224 on the test images to further enhance the corneal glint. In this implementation, the edge enhancement algorithm identifies and enhances the prominence of features within the eye, particularly the glint, having a boundary with other features in the eye. Edges, particularly those around the glint, are highlighted thereby reducing the time needed to focus the imaging system 108 using the method 300 and increasing the image sharpness signal.

Using the recorded 312 test images, the imaging system 108 calculates 316 a defocus measurement for each of the test images to determine the relative degrees of focus/defocus for each test image. Thus, the defocus measurement represents the extent to which a test image is in or out of focus with respect to the iris of the subject. In one example, the imaging system 108 calculates 316 the defocus measurement using a pixel intensity distribution of the corneal glints in the eyes of the subject 100. That is, the pixel intensity distribution is identified for each test image. The defocus measurement of a test image is a function of large spatial gradients in the test images generated by the corneal glint. That is, the higher the spatial rate of change of the pixel intensity, the lower the defocus. This is based on the assumption that a focused glint image has very sharp edges and is the most significant feature in the image. The effect can be enhanced by the optional application of the grayscale transformation described above which reduces artificial edges introduced by the unbalanced color channels in the color sensor.

Having calculated 316 a defocus measurement of a test image at a measurement point, this process is repeated at least two more times, thereby calculating 316 at least two more defocus measurements of corresponding test images at, for example, measurement positions 112A and 112C-112F. In each of the at least two repetitions of the process, the test images are captured at different measurement positions (by varying system optical power) with respect to the ocular areas 104 compared to the first measurement position (e.g., 112B). By recording 312 test images at different measurement positions, each recorded test image differs from the other recorded test images and therefore will typically have different defocus measurements. In some cases, the different measurement positions can be separated by a pre-set amount known to cover a typical physical range within which a face of a subject 100, and therefore the irises of the subject, will be in focus. For example, the different measurement positions can be separated by about 20 mm from each other. In one embodiment, test images are recorded by successively stepping the measurement position in a single direction, by adjusting a focal length of the optical lens 212, from a smallest value to largest value (or vice versa) over a range in which an iris of a subject is expected to be in focus.

An equation is then fit to the measurement positions of the test images as described above and corresponding to measurement positions 112A and 112C, respectively. In other embodiments, additional test images and corresponding measurement positions may be recorded and used in this process. The measurement positions and the corresponding defocus measurements are used to define points in a "coordinate system" of measurement position and defocus measurement. In one example, the equation that is fit to these "coordinates" is a closed-form 2nd-order quadratic equation. The processor 224 solves the equation that is fit to the data for a point at the maximum. This maximum point of the equation is used by the imaging system 108 as the estimated focal point for the ocular area, or more specifically, the iris of the subject 100. The estimated measurement position is the location at which the optical system is estimated to capture an focused iris image of the subject 100 usable for biometric identification (i.e., sufficiently in focus that the musculature of the iris is resolvable).

In one embodiment, once the set of measurement positions 112A-112F has been acquired, the shape of a curve formed by the set of focal points (or a subset thereof) is analyzed to reject bad test images and focal points. The equation of the curve that is fit to the data is typically expected to have a single peak value (corresponding to the facial feature (e.g., the iris) being in focus). The curve is also typically expected to increase monotonically toward the peak and decrease monotonically after the peak. If more than one peak is present in the curve, caused by for example a subject blinking or moving during the recording of a test image, or the corneal glint missing in the captured test image, some or all of the measurement positions may be rejected and optionally replaced. Also, the curve can also be used to determine if the subject is outside the capture range of the imaging system 108. If a curve has a peak at either of its endpoints, the subject is outside of the capture range. In one example, the a curve peak is at a near point (approximately 200 mm) then the subject is too close. If a curve peak is at a far point (approximately 500 mm), then the subject is too far away.

As described above, the estimated focus point is estimated using a finite number of test images and defocus measurements. The larger the number of test images and defocus measurements used to calculate the estimated focal point, the more accurate the estimated focal point will be (i.e., the more focused the image will be). However, this is balanced by the additional time and computational resources required to record additional test images and calculate the estimated focal point based on the additional data. In some situations, the benefit of improved accuracy is not worth the additional time because the conditions under which the images are taken (e.g., an uncooperative subject 100, motion of the subject or of the operator of the system 108) necessitate quickly (e.g., between 0.3 seconds and 1.2 seconds) recording an iris image. Thus, the estimated focal point inherently takes into account that there is a tradeoff between quickly recording an image that is approximately in focus but over a limited amount of time (e.g., a blinking or moving subject) versus the perfect focus that can be achieved assuming infinite time and no motion between the subject and optical system.

Once the imaging system 108 calculates the estimated focal point, the processor 224 of the imaging system sends a control signal to the optical lens 212 to adjust the measurement position accordingly. The optical system then uses the image capture parameters determined earlier in the process to record the iris image.

One advantage of the example method 300 is that it does not require any sophisticated image processing algorithms. Another advantage is that it provides for rapid quality control through analysis of the focus curve, thereby eliminating images in which the subject has moved or blinked (creating multiple maxima in the curve) and recording replacement images.

This embodiment of the imaging system 108 is configured for imaging irises, but as mentioned above the imaging system and the focusing method can be applied to any subject without departing from the present disclosure.

Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
    calculating image capture parameters of an image capture device for an ocular area including at least one eye of a subject, the image capture parameters used for enhancing a corneal glint from the eye, the corneal glint being a specular reflection from a portion of the eye's cornea caused by an illumination source of the image capture device, the enhancing comprising differentiating an intensity of the corneal glint relative to intensities other features in the ocular area using a grayscale transformation to adjust amplitudes from color pixels captured by the image capture device;
    capturing at least three different test images of the ocular area, each of the different test images recorded at a different measurement position thereby indicating a different degree to which the test images are in or out of focus on relative to the corneal glint, the different measurement positions are along an optical axis of the image capture device, and at least one of the different measurement positions producing an out-of-focus test image;
    calculating, for each of the at least three different test images, a defocus measurement based on the corneal glint information from the corresponding test image, each defocus measurement corresponding to a different measurement position;
    determining an estimated focal point of the corneal glint based on the at least three defocus measurements; and
    capturing an iris image of the subject by changing the focal length based on the estimated focal point, the iris image used for biometric identification, wherein the grayscale transformation adjusts the iris image to be linear over a range of grayscale of an iris captured in the iris image and adjusts the iris image to be nonlinear outside of the range.

2. The method of claim 1, wherein the calculating comprises:
fitting an equation to the at least three defocus measurements, wherein the equation comprises a closed-form quadratic equation describing a curve; and
solving the equation for a point at the maximum of the corneal glint information.

3. The method of claim 2 further comprising:
determining whether the curve includes more than one maximum; and
removing at least one rejected test image and at least one corresponding rejected defocus measurement from the curve to reduce the number of maxima of the curve to one maximum.

4. The method of claim 1, wherein the corneal glint information for each corresponding test image includes an intensity distribution having a spatial gradient, and wherein the calculating, for each of the at least three different test images, a defocus measurement based on the corneal glint information includes using a spatial rate of change of pixel intensity distribution of a corneal glint from each of the at least three test images.

5. The method of claim 4, wherein a defocus measurement having a higher spatial rate of change of the pixel intensity indicates a corresponding measurement position that is closer to the estimated focal point of the corneal glint relative to a defocus measurement having a lower spatial rate of change of the pixel intensity.

6. The method of claim 1, wherein enhancing the corneal glint further comprises applying an edge enhancement algorithm.

7. The method of claim 6, wherein the edge enhancement algorithm is an image sharpness algorithm.

8. The method of claim 6, wherein the edge enhancement algorithm comprises:
identifying and enhancing the corneal glint having a boundary with other features in the eye; and
highlighting edges around the corneal glint.

9. The method of claim 1, wherein calculating the image capture parameters includes adjusting a gain of a sensor for enhancing the corneal glint.

10. The method of claim 1, wherein calculating the image capture parameters includes adjusting an integration time of a sensor for enhancing the corneal glint.

11. The method of claim 1, wherein enhancing the corneal glint further comprises applying a grayscale correction to improve signal to noise ratio of the corneal glint.

12. The method of claim 11, wherein the grayscale correction is applied to accentuate edges in the captured test images.

13. The method of claim 1, wherein the grayscale transformation is performed by a transfer function, the transfer function changes contrast to improve detail within an area of an iris captured in the iris image, at the expense of detail in areas outside of the iris.

14. The method of claim 1, wherein the grayscale transformation equalizes amplitudes from color pixels in the color sensor.

15. The method of claim 1, wherein the grayscale transformation reduces artificial edges of the corneal glint.

16. The method of claim 1, wherein a corneal glint captured at the estimated focal point has very sharp edges and suppresses other features of the eye.

17. The system of claim 1, wherein the grayscale transformation is performed by a transfer function, the transfer function changes contrast to improve detail within an area of an iris captured in the iris image, at the expense of detail in areas outside of the iris.

18. The system of claim 1, wherein the grayscale transformation equalizes amplitudes from color pixels in the color sensor.

19. The system of claim 1, wherein the grayscale transformation reduces artificial edges of the corneal glint.

20. A system comprising:
an illumination source for illuminating an ocular area including at least one eye of a subject;
an optical lens having a focal plane and an adjustable focal length;
a sensor substantially disposed in the focal plane of the optical system, the sensor substantially perpendicular to an optical axis of the system, wherein the sensor is configured to capture an image of an iris of the subject;
a processor configured to execute computer-executable instructions stored on a non-transitory computer-readable medium, the instructions when executed causing the processor to perform a method comprising:
calculating image capture parameters of an image capture device for the ocular area, the image capture parameters used for enhancing a corneal glint from the eye used as a focusing feature, the corneal glint being a specular reflection from a portion of the eye's cornea caused by the illumination source, the enhancing comprising differentiating an intensity of the corneal glint relative to intensities other features in the ocular area using a grayscale transformation to adjust amplitudes from color pixels in the sensor of the image capture device;
recording at least three different test images of the ocular area using the sensor, each of the different test images recorded at a different measurement position indicating a different degree to which the test images are in or out of focus proximate to the corneal glint, the different measurement positions are along the optical axis of the optical lens, and at least of one of the different measurements producing an out-of-focus test image;
calculating, for each of the at least three different test images, a defocus measurement based on the corneal glint information from the corresponding test image, each defocus measurement corresponding to a different measurement position;
determining an estimated focal point of the corneal glint based on the at least three defocus measurements; and
capturing an iris image of the subject by changing the focal length based on the estimated focal point using the optical lens and the sensor, the iris image used for biometric identification, wherein the grayscale transformation adjusts the iris image to be linear over a range of grayscale of an iris captured in the iris image and adjusts the iris image to be nonlinear outside of the range.

21. The system of claim 20, further comprising an optical filter for limiting the wavelength of illumination received by the sensor to a range of wavelengths.

22. The system of claim 21, wherein the optical filter is configured to suppress other sources of illumination incident upon the subject for enhancing the corneal glint.

23. The system of claim 20, further comprising a face camera for identifying coordinates for the ocular area and supplying the coordinates to the processor.

24. The system of claim 20, wherein the calculating using the processor further comprises:
fitting an equation to the at least three defocus measurements, wherein the equation comprises a closed-form quadratic equation describing a curve; and
solving the equation for a point at the maximum of the corneal glint information.

25. The system of claim 24, further comprising:
determining whether the curve includes more than one maximum; and
removing at least one rejected test image and at least one corresponding rejected defocus measurement from the curve to reduce the number of maxima of the curve to one maximum.

26. The system of claim 20, wherein the corneal glint information for each corresponding test image includes an intensity distribution having a spatial gradient, and wherein the calculating, for each of the at least three test images, a defocus measurement based on the corneal glint information includes using a spatial rate of change of pixel intensity distribution of a corneal glint from each of the at least three test images.

27. The system of claim 26, wherein a defocus measurement having a higher spatial rate of change of the pixel intensity indicates a corresponding measurement position that is closer to the estimated focal point of the corneal glint relative to a defocus measurement having a lower spatial rate of change of the pixel intensity.

28. The system of claim 20, wherein enhancing the corneal glint further comprises applying an edge enhancement algorithm.

29. The system of claim 28, wherein the edge enhancement algorithm is an image sharpness algorithm.

30. The system of claim 28, wherein the edge enhancement algorithm comprises:
identifying and enhancing the corneal glint having a boundary with other features in the eye; and
highlighting edges around the corneal glint.

31. The system of claim 20, wherein calculating the image capture parameters includes adjusting a gain of a sensor for enhancing the corneal glint.

32. The system of claim 20, wherein enhancing the corneal glint further comprises applying a grayscale correction to improve signal to noise ratio of the corneal glint.

33. The system of claim 32, wherein the grayscale correction is applied to accentuate edges in the captured test images.

34. The system of claim 20, wherein a corneal glint captured at the estimated focal point has very sharp edges and suppresses other features of the eye.

* * * * *

UNITED STATES PATENT AND TRADEMARK OFFICE
CERTIFICATE OF CORRECTION

PATENT NO.       : 9,911,036 B2
APPLICATION NO.  : 13/783838
DATED            : March 6, 2018
INVENTOR(S)      : Keith W. Hartman It is certified that error appears in the above-identified patent and that said Letters Patent is hereby corrected as shown below:

In the Claims

Column no: 10, Line(s) no: 41-42, Claim 1, "intensities other features" to read as --intensities of other features--.
Column no: 11, Line(s) no: 56, Claim 13, "an iris" to read as --the iris--.
Column no: 11, Line(s) no: 63, Claim 16, "a corneal glint" to read as --the corneal glint--.
Column no: 11, Line(s) no: 66, Claim 17, "The system of claim 1" to read as --The method of claim 1--.
Column no: 12, Line(s) no: 04, Claim 18, "The system of claim 1" to read as --The method of claim 1--.
Column no: 12, Line(s) no: 07, Claim 19, "The system of claim 1" to read as --The method of claim 1--.
Column no: 12, Line(s) no: 16, Claim 20, "optical system" to read as --optical lens--.
Column no: 12, Line(s) no: 18-19, Claim 20, "subject; a processor" to read as --subject; and a processor--.
Column no: 12, Line(s) no: 30, Claim 20, "intensities other features" to read as --intensities of other features--.
Column no: 14, Line(s) no: 22, Claim 34, "a corneal glint" to read as --the corneal glint--.

Signed and Sealed this
Second Day of October, 2018

Andrei Iancu
*Director of the United States Patent and Trademark Office*